United States Patent [19]

Shymon

[11] Patent Number: 4,574,081
[45] Date of Patent: Mar. 4, 1986

[54] ANTIPLAQUE DENTIFRICE HAVING IMPROVED FLAVOR

[75] Inventor: Stephen J. Shymon, Metuchen, N.J.

[73] Assignee: Colgate-Palmolive Co., New York, N.Y.

[21] Appl. No.: 654,351

[22] Filed: Sep. 25, 1984

[51] Int. Cl.$^4$ .......................... A61K 7/18; A61K 7/22
[52] U.S. Cl. ......................................... 424/52; 424/54
[58] Field of Search ..................................... 424/49–58

[56] References Cited

U.S. PATENT DOCUMENTS

| | | | |
|---|---|---|---|
| 1,488,097 | 3/1924 | Creger | 424/58 |
| 2,888,383 | 5/1969 | Byrne | 424/54 |
| 2,984,639 | 5/1961 | Stamberger et al. | 260/32.4 |
| 3,325,402 | 6/1967 | Erskine | 210/64 |
| 3,431,208 | 3/1969 | Bailey | 252/106 |
| 3,491,135 | 1/1970 | Krueger et al. | 260/448 |
| 3,703,583 | 11/1972 | Martin | 424/54 |
| 3,842,168 | 10/1974 | Colodney | 424/52 |
| 3,843,779 | 10/1974 | Norfleet | 424/54 |
| 3,864,472 | 2/1975 | Pensak et al. | 424/54 |
| 3,988,425 | 10/1976 | Jockel et al. | 423/415 A |
| 4,118,476 | 10/1978 | Gaffar et al. | 424/54 |
| 4,188,372 | 2/1980 | Gaffar | 424/54 |
| 4,363,795 | 12/1982 | Wahlstam | 424/54 |
| 4,490,353 | 12/1984 | Crawford et al. | 424/52 |

FOREIGN PATENT DOCUMENTS 1319396 6/1973 United Kingdom .

OTHER PUBLICATIONS

Arctander (1960) Perfume & Flavor Materials of Natural Origin, pp. 67, 412–415, 513–516.
Arctander (1969) Perfume & Flavor Chemicals I–236, II–1839, 1840, 1841, 1842.
"Quaternary Ammonium and Related Compounds" in the article on Antiseptics and Disinfectants in Kirk-Othmer Encyclopedia of Chemical Technology, 2nd edition (vol. 2, pp. 632–635).

*Primary Examiner*—Shep K. Rose
*Attorney, Agent, or Firm*—Robert L. Stone; Murray M. Grill; Herbert S. Sylvester

[57] ABSTRACT

An antiplaque dentifrice having improved flavor comprising an antiplaque quaternary ammonium compound, a flavoring agent consisting essentially of at least 15% by weight of anethol, up to 46% by weight of menthol and up to 39% by weight of peppermint, and a sweetening agent in the weight ratio of about 6:1 to 1.3:1 flavoring agent:sweetening agent, in a dental vehicle comprising a dental abrasive.

19 Claims, No Drawings

ANTIPLAQUE DENTIFRICE HAVING IMPROVED FLAVOR

BACKGROUND AND PRIOR ART

The present invention relates to the formulation of a quarternary ammonium-containing antiplaque dentifrice with improved taste, that is sweet, pleasant, cool and reduces the bitter taste of the quaternary ammonium compound, containing a flavoring agent consisting essentially of at least 15% by weight of anethol, up to 46% by weight of menthol and up to 39% by weight of peppermint, and a sweetening agent in the weight ratio of about 6:1 to 1.3:1, preferably 2.5:1, flavoring agent:sweetening agent.

It has been found that a dentifrice flavor consisting essentially of specified amounts of anethol, menthol and peppermint significantly improves the taste of a quaternary ammonium based antiplaque dentifrice. It has additionally been found that the presence of said sweetening agent in aforesaid ratio synergistically improves the taste of the flavor in the dentifrice.

The ability of quaternary ammonium compounds to inhibit the formation of dental plaque is well documented. These compounds, however, are bitter, and this markedly reduces the consumer acceptability of antiplaque dentifrice containing quaternary ammonium compounds.

Accordingly, sweeteners such as sodium saccharin, and flavoring oils including oils of spearmint, peppermint, wintergreen, sassafras, clove, sage, eucalyptus, marjoram, cinnamon, lemon and orange, as well as methylsalicylate have been conventionally used in dentifrices to improve the flavor, as shown in U.S. Pat. No. 3,842,168; No. 3,843,779; No. 4,118,476 and No. 4,188,372. Despite the reduction of the bitterness of the quaternary ammonium compounds afforded by aforesaid flavors, the taste of these dentifrices lacks consumer appeal and may even be offensive, due to either insufficient masking of the bitterness or too strong a flavor. U.S. Pat. No. 3,988,425 has solved the bitterness problem attributed to the presence of quaternary ammonium compounds in dentifrices by reacting dihydrochalcone glucosides with certain quaternary ammonium compounds to give the corresponding quaternary ammonium derivatives which have a sweet taste and are bactericidal in nature.

U.S. Pat. No. 3,864,472 discloses a lemon flavored mouthwash, containing a quaternary ammonium antibacterial compound and a lemon oil flavorant.

U.S. Pat. No. 3,491,135 discloses that salts of (3-cyclohexyl-3-hydroxy-3-phenylpropyl) triethylammonium ion and pamoic acid show little or none of the extremely bitter taste of the corresponding quaternary ammonium halide compound. The pamoates thereof are said to have unobjectionable flavors.

None of the above cited prior art discloses an antiplaque dentifrice having significantly improved taste, comprising a flavoring agent formulation which contains specificed amounts of anethol, menthol and peppermint, which when added in amounts close to about 1% by weight (e.g. about 0.8-1.2%), to a quaternary ammonium-containing antiplaque dentifrice, greatly reduce the bitterness of said dentifrice, and improve the taste thereof.

SUMMARY OF THE INVENTION

It has now been found that the flavor of dental cream formulations containing antiplaque quaternary ammonium compounds can be significantly improved, and the bitter taste of said quaternary ammonium compound is substantially reduced by adding a flavoring agent formulation consisting essentially at least 15% by weight of anethol, up to 46% by weight of menthol and up to 39% by weight of peppermint, and a sweetening agent in the weight ratio of about 6:1 to 1.3:1, preferably 2.5:1, respectively, flavoring agent:sweetening agent.

Accordingly, a primary object of the present invention is to provide a better tasting antiplaque dentifrice based on quaternary ammonium active ingredients, by the incorporation of a flavoring agent formulation containing anethol, menthol and peppermint in specified amounts.

Another object of this invention is to provide an antiplaque dentifrice with improved flavor also containing a sweetening agent which synergistically improves the flavor of the dentifrice.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the novel antiplaque dentifrice having improved taste of this invention comprises as the essential ingredients, an effective amount of an antiplaque quaternary ammonium compound, a flavoring agent formulation consisting essentially of at least 15% by weight of anethol, up to 46% by weight of menthol and up to 39% by weight of peppermint, and a sweetening agent in the weight ratio of about 6:1 to 1.3:1, preferably 2.5:1, flavoring agent:sweetening agent, in a dental vehicle comprising a dental abrasive.

More specifically, present invention relates to an antiplaque dentifrice formulation with improved flavor comprising an effective antimicrobial amount of a quaternary ammonium compound, about 0.8-1.2% by weight of a flavoring agent formulation which flavoring agent typically consists essentially of about 15-45% anethol, about 46-31% menthol and about 39-24% peppermint, and about 0.2-0.6% sweetening agent, in the weight ratio of about 6:1 to 1.3:1, preferably 2.5:1, flavoring agent:sweetening agent, in a dental vehicle comprising a dental abrasive. The present antiplaque dentifrice preferably contains about 1.5-5% by weight of a betaine surfactant, about 18-30% by weight humectant including polyethylene glycol, sorbitol, glycerin and mixtures thereof, 0.5-2% by weight nonionic gelling agent and about 0.05-2% by weight of a fluoride-providing compound in an aqueous vehicle containing about 35-65% by weight of a water-insoluble dental abrasive. All of the aforesaid preferred ingredients are compatible with the quaternary ammonium compound, the flavor formulation and the sweetening agent.

Cationic antibacterial materials are well known in the art. See, for instance the section on "Quaternary Ammonium and Related Compounds" in the article on "Antiseptics and Disinfectants" in Kirk-Othmer Encyclopedia of Chemical Technology, 2nd edition (Vol. 2 pp. 632-635), incorporated herein by reference. Cationic materials which possess antibacterial activity (i.e. are germicides) are used against bacteria and have been used in oral compositions to counter plaque formation caused by bacteria in the oral cavity.

Among the most common of these antibacterial antiplaque quaternary ammonium compounds is benzethonium chloride (BTC), also known as Hyamine 1622 or diisobutylphenoxyethoxyethyl dimethyl benzyl ammonium chloride, and cetyl pyridinium chloride. In an oral preparation this material is highly effective in promoting oral hygiene by reducing formation of dental plaque and calculus, which is generally accompanied by a reduction in periodontal diseases. Other cationic antibacterial agents of this type are those mentioned, for instance, in U.S. Pat. Nos. 2,984,639, 3,325,402, 3,431,208 and 3,703,583, and British Pat. No. 1,319,396.

Other antibacterial antiplaque quaternary ammonium compounds include those in which one or two of the substituents on the quaternary nitrogen has a carbon chain length (typically alkyl group) of some 8 to 20, typically 10 to 18, carbon atoms while the remaining substituents have a lower number of carbon atoms (typically alkyl or benzyl group), such as 1 to 7 carbon atoms, typically methyl or ethyl groups. Dodecyl trimethyl ammonium bromide, benzyl dimethyl stearyl ammonium chloride, cetyl pyridinium chloride and quaternized 5-amino-1,3-bis(2-ethylhexyl)-5-methyl hexa hydro-pyrimidine are typical quaternary ammonium antibacterial agents.

The dentifrice formulation of present invention contains an effective amount of the antiplaque quaternary ammonium compound, preferably about 0.01-5%, and most preferably 0.025-1% by weight of the composition.

The ability of quaternary ammonium compounds to inhibit the formation of dental plaque is well known. However, the bitterness of these compounds is also well known. As a matter of fact, the bitterness of a BTC rinse is minimal to non-existent, while the bitterness of the BTC dentifrice is robust. This is so, even though the amount of BTC delivered to the mouth is greater from the rinse than from the dentifrice. Accordingly, the bitterness problem is specific to dentifrices containing BTC or other quaternary antiplaque agents.

It has now been found that the incorporation of present novel flavoring agent formulation consisting essentially of specified amounts of anethol, menthol and peppermint into antiplaque dental formulations based on quaternary active ingredients in proper ratio to sweetening agent, unexpectedly and significantly improves the taste of this dentifrice, and reduces the bitter taste of the quaternary ammonium-containing dentifrice. Dentifrices containing this novel flavoring agent formulation have a positive initial impact upon tasting, whereas dentifrices containing other flavors presently on the market can be initially offensive, or have a medicinal flavor.

The selected components of present novel flavoring agent formulation typically consists essentially of a mixture of:

1. about 15-45% and preferably 25-45% by weight anethol, MeO.C$_6$H$_4$.CH:CHMe, a sweet aromatic semi-liquid;

2. about 46-31% and preferably 41-31% by weight menthol, 3-hydroxymenthane, cool tasting colorless crystals; and 3. about 39-24% and preferably 34-24% by weight peppermint in the form of dried leaves, a fluid extract or an oil, usually a colorless liquid of a strong agreeable odor. The aforedefined three components are mixed together and the mixture is added to the dentifrice. This mixture in combination with a sweetening agent effectively masks the bitter taste of the quaternary compound.

Specific flavoring agent formulations utilized herein are:

|  | A (%) | B (%) | C (%) | D (%) |
| --- | --- | --- | --- | --- |
| Anethol | 25 | 15 | 35 | 45 |
| Menthol | 41 | 46 | 36 | 31 |
| Peppermint | 34 | 39 | 29 | 24 |

It has been found that reducing the anethol content below 15%, and increasing the menthol content above 46%, and the peppermint content above 39% provides poor coverage of the bitterness due to the quat BTC (benzethonium chloride); whereas flavoring agent formulations A-D inclusive in proper ratio to sweetening agent provide good coverage of the BTC bitterness in the dentifrice.

The amount of present novel flavoring agent formulation effective in masking the bitterness of the quat, and yield a non-medicinal, pleasant tasting flavor, is typically about 0.8 to 1.2% by weight of the dentifrice composition. Greater amounts of flavor produce a strong flavor and lesser amounts yield a weak flavor.

Another essential ingredient in present invention is the sweetening agent in the weight ratio of about 6:1 to 1.3:1, and preferably 2.5:1 of flavoring agent: sweetening agent. The sweetening agent which is desirably at least as sweet as sucrose, includes sucrose, lactose, maltose, stevioside, perillartine, acetosulfam, sodium cyclamate and sodium saccharin, coacts with the flavoring agent in the production of a sweet, cool pleasant taste which masks or covers the bitterness of the quaternary compound. The amount of sweetening agent effective in assisting the present novel flavor formulation in masking the bitterness of the quat and sweetening the dentifrice is typically about 0.2-0.6% and preferably about 0.4% by weight of the dentifrice composition. Less than 0.2% does not sufficiently cover the bitterness of the quat and greater than 0.6% produces a dentifrice having a strong sweet taste.

The present antiplaque dentifrice preferably contains a surfactant to promote foaming. It is preferable to employ betaine surfactants because it improves the foaming of these formulations without deactivating the quaternary antibacterial agents.

The betaine component of present dentifrice composition has the general formula:

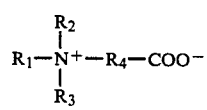

wherein R$_1$ is an alkyl group having 10 to about 20 carbon atoms, preferably 12 to 16 carbon atoms or the amido radical:

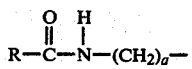

wherein R is an alkyl group having about 10 to 20 carbon atoms and a is the integer 1 to 3; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl betaine or 2-(N-decyl-N,N-dimethylammonio) acetate, coco betaine or 2-(N-coco-N,N-dimethylammonio) acetate, myristyl betaine, palmityl betaine, lauryl betaine, cetyl betaine, stearyl betaine, etc. The amidobetaines similarly include cocoamidoethyl betaine, cocoamidopropyl betaine, lauramidopropyl betaine and the like.

The betaines, which are zwitterionic materials, function as a foaming agent in the quaternary-containing dentifrice compositions. They act cationically over a wide pH range, but do not deactivate the quateranry antimicrobial activity.

In addition to the non-interference exhibited by the betaines with the quaternary activity, laboratory foam tests have shown that formulations containing both the quaternary ammonium compound (quat) and the betaine, foam 2-3 times better than the nonionic/quat formulations.

The zwitterionic betaines are completely compatible with the quaternary antimicrobial antiplaque agents, the novel flavor formulation containing specified amounts of anethol, menthol and peppermint, and the sweetening agent, and impart detersive and improved foaming properties to the quaternary-containing dentifrice composition without deactivating the antimicrobial properties thereof. The amount of betaine effective in the production of improved foaming may be varied from about 1.5-5% by weight of the total formulation.

Cosmetic problems of stability is incurred with all zwitterionic-containing dentifrices, such as crimp leakage of flavor. The flavor oozes and is not solubilized in the zwitterionic surfactant. However, stability evaluations of present novel antiplaque dentifrices containing glycerin and/or sorbitol humectant indicate satisfactory flavor stability for nine weeks aging at 49° C.

In a toothpaste, the dental vehicle is a liquid vehicle comprising water, and a humectant selected from the group consisting of glycerin, sorbitol, polyethylene glycol and mixtures thereof. The humectant system constitutes about 18-30% by weight of the total composition.

Another preferable ingredient in present dentifrice is a gelling agent which is a nonionic gum, in an amount up to 5% by weight and preferably about 0.5-2%. It has been found that large organic anionic molecules such as carboxymethylcellulose have the potential to deactivate the quaternary antibacterial activity. Accordingly, hydroxyethylcellulose, which is a nonionic small organic molecule, effects a stable pituitous gel in the betaine-quat system of present invention, and is the preferred gelling agent. Other nonionic gelling agents may be used such as hydroxymethylcellulose, and the like.

The fluoride-providing compounds, which are preferably additional ingredients in present dentifrice, are characterized by their ability to release fluoride ions in water and by substantial freedom from reaction with other compounds of the dentifrice. Among these materials are inorganic fluoride salts, such as soluble alkali metal, alkaline earth metal and heavy metal salts, for example, sodium fluoride, potassium fluoride, ammonium fluoride, lead fluoride, a copper fluoride such as cuprous fluoride, zinc fluoride, a tin fluoride such as stannic fluoride or stannous chlorofluoride, barium fluoride, sodium fluorosilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluoride-providing compound is dependent to some extent, upon the type of compound, its solubility, and the dentifrice, but it must be a non-toxic amount. In a solid oral preparation, such as a toothpaste or dental cream, an amount of such compound which releases a maximum of 1% by weight of the preparation is considered satisfactory. Any suitable minimum amount of such compound may be used, but it is preferable to employ sufficient compound to release from 0.005% to 1%, and preferably about 0.1% of fluoride ion. Typically, in the cases of alkali metal fluorides and stannous fluoride, this component is present in an amount up to 2% by weight, based on the weight of the preparation. In the case of sodium monofluorophosphate, the compound may be present in an amount up to 7.6% by weight, more typically 0.76%.

The dentifrice prepared in accordance with this invention, contains conventional water-insoluble polishing materials or dental abrasives, generally in amounts from 35-65% by weight of the total formulation. Suitable examples of dental abrasives or polishing materials include sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, zirconium silicates, bentonite, and mixtures thereof. The preferred abrasives are alumina-containing abrasives such as calcined alumina and hydrated alumina and mixtures thereof.

The dentifrice of this invention may also contain conventional additional ingredients such as coloring or whitening agents, and preservatives. These additional ingredients may each be added to the dentifrice in minimal amounts of up to 5% by weight, and preferably up to 1%, provided they do not interfere with the foaming, antiplaque and compatibility properties of the finished product.

The dentifrice of this invention is prepared by conventional methods of making toothpaste and/or dental creams. More specifically, a toothpaste may be prepared by forming a gel with the nonionic gelling agent and water, adding sequentially thereto with mixing the powdered materials including the fluoride compound, the quaternary ammonium compound and sweetening agent, and humectant, followed by the addition with mixing of polishing agent and the betaine and flavor, and tubing the final mixture.

Another method of preparing the dentifrice of this invention is specifically set forth and claimed in a copending patent application, and comprises the preparation of two separate gel phases, an oil gel phase of the active quaternary ingredient solubilized in the betaine surfactant and the flavor, a water gel phase of water, humectant, nonionic gelling agent, the fluoride salt and the sweetening agent, combining these two gel phases into a single gel, and adding a dental abrasive thereto as a final step, or adding said abrasive to the water gel phase prior to the addition of the oil gel phase.

In the practice of this invention to promote oral hygiene, the dentifrice according to this invention is applied regularly to dental enamel by brushing the teeth for 30-90 seconds at least once daily.

DETAILED DESCRIPTION OF THE INVENTION

The following examples are further illustrative of the nature of the present invention, but it is understood that the invention is not limited thereto. The compositions are prepared in the usual manner and all amounts and proportions referred to herein and in the appended claims are by weight unless otherwise indicated.

EXAMPLE 1

Glycerin Humectant Anti-Plaque Dentifrice

| Ingredients | % |
| --- | --- |
| Water (Deionized) | 19.34 |
| Sodium Saccharin | 0.30 |
| Sodium Monofluorophosphate | 0.76 |
| Hydroxyethylcellulose | 1.10 |
| Glycerin | 20.00 |
| Benzethonium Chloride | 0.50 |
| Flavor Formulation[1] | 1.00 |
| Cocamidopropyl Betaine | 5.00 |
| Calcined Alumina | 10.00 |
| Hydrated Alumina | 42.00 |

[1]25% anethol, 41% menthol and 34% peppermint

The benzethonium chloride is dispersed in the flavor and this dispersion is mixed into the betaine to form an oil gel. The sodium saccharin and sodium monofluorophosphate (MFP) are dissolved in the water. Hydroxyethylcellulose is dispersed in the glycerin, and this mixture is added to the water-saccharin-MFP solution with stirring to form a water gel. The oil and water gels are mixed to form a stable parent gel. The calcined alumina and hydrated alumina are admixed with the parent gel to produce the finished antiplaque dentifrice having a sweet, cool, pleasant flavor and good BTC (bitterness) coverage, and a positive initial impact upon tasting, and possesses excellent chemical and cosmetic stability and sufficient foaming properties. This dentifrice is prepared at room temperature.

EXAMPLE 2

Example 1 is repeated except that 20% sorbitol is substituted for the 20% glycerin. The resultant product is equally effective against plaque related bacteria and also has a sweet, cool, pleasant taste and good BTC coverage, and a positive initial impact upon tasting, and possesses excellent chemical and cosmetic stability and sufficient foaming properties.

EXAMPLES 3-6

Example 1 is repeated except that the level of sodium saccharin is varied from 0.2% to 0.6% and the water content is adjusted accordingly.

| Ex. | Saccharin (%) | Taste Evaluation |
| --- | --- | --- |
| 3 | 0.2 | Covers BTC, fair |
| 1 | 0.3 | Covers BTC, Fair to Good |
| 4 | 0.4 | Good, Ideal |
| 5 | 0.5 | Good, Sweet |
| 6 | 0.6 | Good, Very Sweet |

EXAMPLES 7-10

Example 4 is repeated except that the level of the flavor is varied from 0.6% to 1.4% and the water content is adjusted accordingly.

| Ex. | Flavor (%) | Taste Evaluation |
| --- | --- | --- |
| 7 | 0.6 | Flavor weak, BTC coverage Fair |
| 8 | 0.8 | Flavor O.K., BTC coverage Fair to Good |
| 4 | 1.0 | Flavor O.K., BTC coverage Good |
| 9 | 1.2 | Flavor Strong, BTC coverage Good |
| 10 | 1.4 | Flavor too Strong, BTC coverage Good |

EXAMPLE 11

Example 4 is repeated except that the flavor formulation contains 15% anethol, 46% menthol and 39% peppermint. The finished product has good BTC coverage.

EXAMPLE 12

Example 4 is repeated except that the flavor formulation contains 35% anethol, 36% menthol and 29% peppermint. The finished product has good BTC coverage.

EXAMPLE 13

Example 4 is repeated except that the flavor formulation contains 45% anethol, 31% menthol and 24% peppermint. The finished product has good BTC coverage.

EXAMPLE 14

| Ingredients | % |
| --- | --- |
| Hydroxyethylcellulose | 1.0 |
| Carbowax 600[1] | 20.0 |
| Na Saccharin | 0.2 |
| MFP[2] | 0.76 |
| CAB[3] (35% A.I.) | 3.5 |
| Dicalcium Phosphate | 49.0 |
| BTC[4] | 0.5 |
| D.I. H$_2$O | 24.04 |
| Flavor Formulation[5] | 1.0 |

[1]Polyethylene glycol, mol. weight 600
[2]Sodium monofluorophosphate
[3]Cocoamidopropyl betaine
[4]Benzethonium chloride
[5]25% Anethol, 41% Menthol and 34% Peppermint The hydroxyethylcellulose and water are premixed for 10 minutes to form a gel. The powdered materials MFP, BTC and saccharin, and the Carbowax humectant is added to the gel and mixed for 10 to 20 minutes. The gelled mixture is added to dicalcium phosphate and mixed for 20 minutes at speed 8 in the Ross agitator. The betaine and flavor is added to the mixture and mixed for 5 minutes at speed 6 in the Ross agitator. The resultant dental cream which is cosmetically attractive is tubed.

The resultant antiplaque product has a very pleasant, sweet, cool taste and the bitterness of the quat compound is completely masked or covered.

EXAMPLE 15

| Ingredients | % |
|---|---|
| Hydroxyethylcellulose | 1.1 |
| Na Saccharin | 0.3 |
| BTC | 0.5 |
| MFP | 0.76 |
| Carbowax 600 | 10.0 |
| Sorbitol (70%) | 10.0 |
| H₂O Deionized | 19.34 |
| Hydrated Alumina | 10.0 |
| Calcined Alumina | 42.0 |
| Flavor Formulation[1] | 1.0 |
| CAB (30% A.I.) | 5.0 |

[1] 25% anethol, 41% menthol and 34% peppermint

The resultant antiplaque dentifrice has a good flavor when initially tasting as well as during the entire period of its use.

EXAMPLE 16

| Ingredients | % |
|---|---|
| Polyethylene Glycol (Carbowax 600) | 15 |
| Glycerin | 5 |
| Hydroxyethylcellulose | 1.10 |
| Sodium Monofluorophosphate | 0.76 |
| Sodium Saccharin | 0.30 |
| Benzethonium chloride (BTC) | 0.50 |
| Hydrated Alumina | 42 |
| Calcined Alumina | 10 |
| CAB (30% A.I.) | 5 |
| Flavor Formulation[1] | 1 |
| Water | 19.34 |
| Fl⁻ content* | 0.07 |

[1] 25% anethol, 41% menthol and 34% peppermint
*Chemical stability of the above formulations after accelerated aging for 12 weeks at 37.8° C. as determined by the percentage of Fl⁻ content This antiplaque dentifrice has a sweet, pleasant, cool flavor and is free of the bitter taste of the BTC antiplaque agent.

Variations in the above formulations may be made. For example, other betaines such as lauramidopropyl betaine, cocobetaine and the like may be substituted for the cocoamidopropyl betaine in the examples. Similarly, other abrasives may be substituted for the specific abrasives in the examples. Likewise, other fluoride-containing compounds such as sodium fluoride, potassium fluoride, etc., may be substituted for the sodium monofluorophosphate in the specific examples. Likewise, cetyl pyridinium chloride or other quaternary ammonium antiplaque agents may be substituted for the benzethonium chloride. Also, sodium cyclamate may replace sodium saccharin.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

I claim:

1. An antiplaque dentifrice having improved flavor comprising as the essential ingredients, an effective amount of at least about 0.01% by weight antiplaque quaternary ammonium compound, said dentifrice being devoid of a fluoride-providing compound or containing a fluoride-providing compound in amount which provides about 0.005-1% by weight of fluoride ion, about 0.8-1 2% by weight of a flavoring agent formulation consisting essentially of from at least 15% up to 45% by weight of anethol, from at least 31% up to 46% by weight of menthol and from at least 24% up to 39% by weight of peppermint, and about 0.2-0.6% by weight of a sweetening agent in the weight ratio of about 6:1 to 1.3:1 flavoring agent:sweetening agent, in a dental vehicle comprising about 35-65% by weight of a water-insoluble dental abrasive and humectant containing about 18-30% by weight of at least one of glycerin, sorbitol and polyethylene glycol and about 0.5-5% by weight of a nonionic gelling agent.

2. The dentifrice according to claim 1, wherein said sweetening agent is at least as sweet as sucrose.

3. The dentifrice according to claim 2, wherein said sweetening agent is selected from the group consisting of sucrose, lactose, maltose, stevioside, perillartine, acetosulfam, sodium cyclamate and sodium saccharin.

4. The dentifrice according to claim 3, wherein said sweetening agent is sodium saccharin.

5. The dentifrice according to claim 1, containing about 1.5-5% by weight of betaine surfactant.

6. The dentifrice according to claim 1, containing about 0.5-2% by weight of said nonionic gelling agent.

7. The dentifrice according to claim 6, containing a fluoride-providing compound in amount which releases about 0.005-1% by weight of fluoride ion.

8. The dentifrice according to claim 1, wherein the antiplaque agent is benzethonium chloride in an amount of about 0.01-5% by weight of the dentifrice.

9. The dentifrice according to claim 2, wherein the ratio of flavoring agent:sweetening agent is 2.5:1 by weight.

10. The dentifrice according to claim 5, wherein the betaine is cocoamidopropyl betaine.

11. The dentifrice according to claim 1, wherein the dental vehicle is a liquid vehicle comprising water and a humectant selected from the group consisting of glycerin, sorbitol, polyethylene glycol and mixtures thereof.

12. The dentifrice according to claim 6, wherein the nonionic gelling agent is hydroxyethylcellulose.

13. The dentifrice according to claim 7, wherein the fluoride-providing compound is sodium monofluorophosphate.

14. The dentifrice according to claim 11, wherein the dental abrasive is an alumina-containing abrasive.

15. The dentifrice according to claim 14, wherein the dental abrasive is a mixture of calcined alumina and hydrated alumina.

16. The dentifrice according to claim 6, wherein the flavor formulation contains 25% anethol, 41% menthol and 34% peppermint.

17. The dentifrice according to claim 6, wherein the flavor formulation contains 15% anethol, 46% menthol and 39% peppermint.

18. The dentifrice according to claim 6, wherein the flavor formulation contains 35% anethol, 36% menthol and 29% peppermint.

19. The dentifrice according to claim 6, wherein the flavor formulation contains 45% anethol, 31% menthol and 24% peppermint.

* * * * *